United States Patent [19]
Wheeler et al.

[11] Patent Number: 5,808,540
[45] Date of Patent: Sep. 15, 1998

[54] POSITION SENSING AND SIGNALING SYSTEM

[76] Inventors: M. Rex Wheeler, 2820 Hope St., Apt. H, Carlsbad, Calif. 92008; Michael G. Bell, 8102 Pageant St., Downey, Calif. 90242; Shawn R. Hill, 6118 Hazzelbrook Ave., Lakewood, Calif. 90712

[21] Appl. No.: 506,090

[22] Filed: Nov. 20, 1995

[51] Int. Cl.$^6$ ............................................ H01C 13/00
[52] U.S. Cl. ........................ 338/114; 73/335.05; 73/774
[58] Field of Search .............................. 338/35, 34, 111, 338/113, 114, 36, 47, 99, 101; 324/694; 252/963; 482/8; 73/774, 335.05

[56] References Cited

U.S. PATENT DOCUMENTS

| | | | |
|---|---|---|---|
| 1,134,320 | 4/1915 | Drew | 128/721 |
| 3,451,032 | 6/1969 | Tempel | 73/774 |
| 3,509,296 | 4/1970 | Harshman et al. | 73/774 |
| 3,517,999 | 6/1970 | Weaver | 128/782 |
| 3,629,774 | 12/1971 | Crites | 338/114 |
| 3,686,606 | 8/1972 | Thoma | 338/35 |
| 3,782,368 | 1/1974 | Reibold | 128/721 |
| 3,820,529 | 6/1974 | Gause et al. | 73/774 |
| 3,942,516 | 3/1976 | Glynn et al. | 128/733 |
| 4,055,078 | 10/1977 | D'Antonio et al. | 73/774 |
| 4,152,304 | 5/1979 | Tadewald | 252/506 |
| 4,170,225 | 10/1979 | Criglar et al. | 128/733 |
| 4,258,100 | 3/1981 | Fujitani et al. | 338/114 |
| 4,419,653 | 12/1983 | Waigand | 338/114 |
| 4,526,039 | 7/1985 | Ceccon et al. | 73/774 |
| 4,634,404 | 1/1987 | Takano | 474/11 |
| 4,696,307 | 9/1987 | Montgieux | 128/782 |
| 5,060,527 | 10/1991 | Burgess | 338/47 |
| 5,152,170 | 10/1992 | Liu | 73/317 |
| 5,174,718 | 12/1992 | Lampeter et al. | 416/48 |
| 5,243,871 | 9/1993 | Weiten | 74/473 |
| 5,436,622 | 7/1995 | Gutman et al. | 340/825.46 |
| 5,536,568 | 7/1996 | Teruo | 338/47 |

Primary Examiner—V. Miller
Assistant Examiner—Robert N. Wieland

[57] ABSTRACT

In a biofeedback device adapted for sensing position of the Transverse Abdominis Muscle (TAM) on small excursions of the abdominal wall including a sensor which changes resistance on a change in dimension thereof in any direction. The sensor element includes a plurality of interlaced electrodes in juxtaposition with a resilient antistatic device. A particular implementation is in the form of a two pole sensor incorporated into a bio-feedback monitor. The sensor is physically attached to the monitor which can be worn on the belt or at or near the waist line. A lever on the back of the monitor rests against the body and engages the sensor comprising a variable resistance foam component. Pressure exerted against the lever, when the TAM is relaxed causes a change in the resistance which energizes the electrical circuit above a given threshold and causes a variable pitch sound to be generated or alternatively drives an electrical vibrator motor at a variable speed. The variation in pitch or vibrator speed is directly related to the amount of pressure exerted on the lever. Thus the wearer of the device can pull in the TAM and eliminate the signal or the vibration and thereby improve his or her general physical condition. The biofeedback device is adapted so that the lever may be bypassed or removed and a variety of different types of anti-static foam sensors may attached or otherwise interconnected to the electrical circuit in place of the lever to be utilized for other purposes. One of these is a constrictor muscle sensor which may be used to sense pressure exerted when exercising such muscles. Other forms of the devices contemplated by this invention, the sensor may comprise a plurality of electrodes connected to a plurality of poles to measure changes in pressure at different locations or in a different dimension. Another feature of the invention is that the sensor is also adapted to sense a change in humidity and thus may be used as a mask or places in close proximity to a changing humidity such as in the path of a patients breathing so that changes in inhaling or exhaling may be monitored.

19 Claims, 5 Drawing Sheets

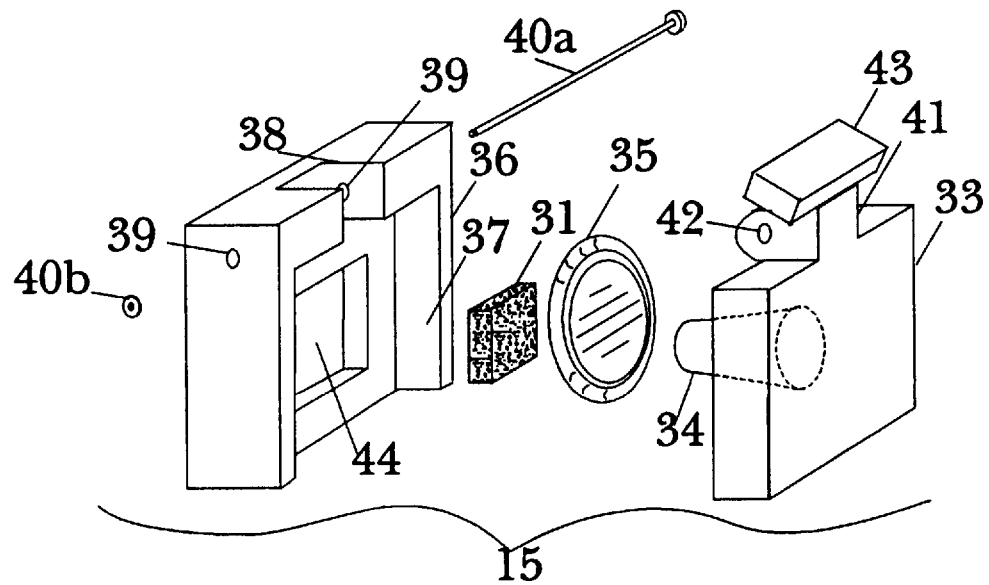
FIGURE 3
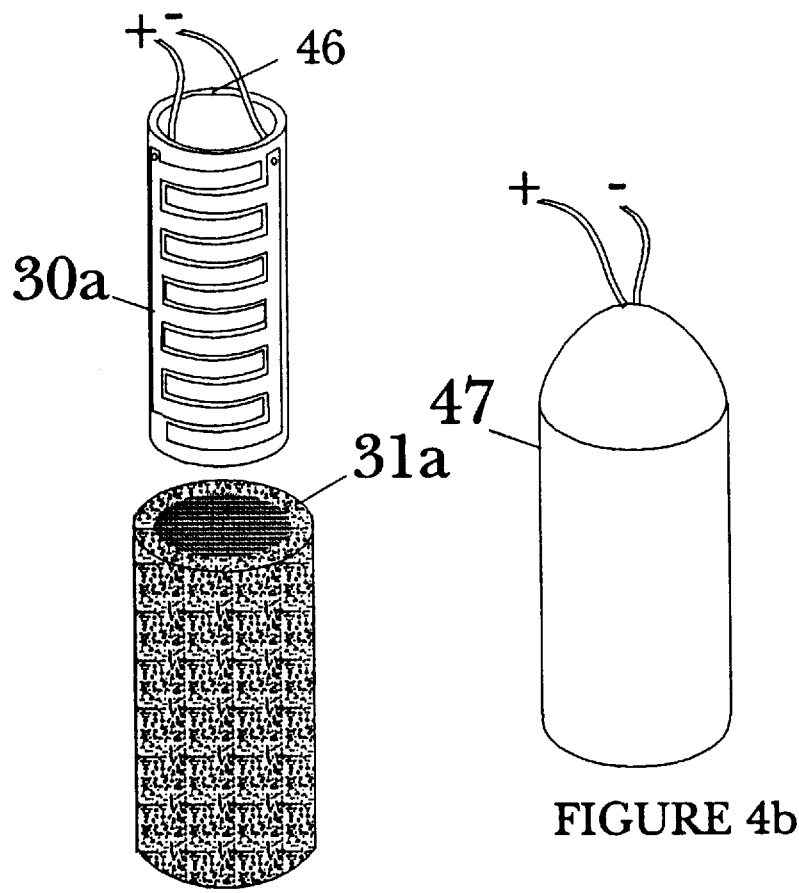
FIGURE 4a
FIGURE 4b

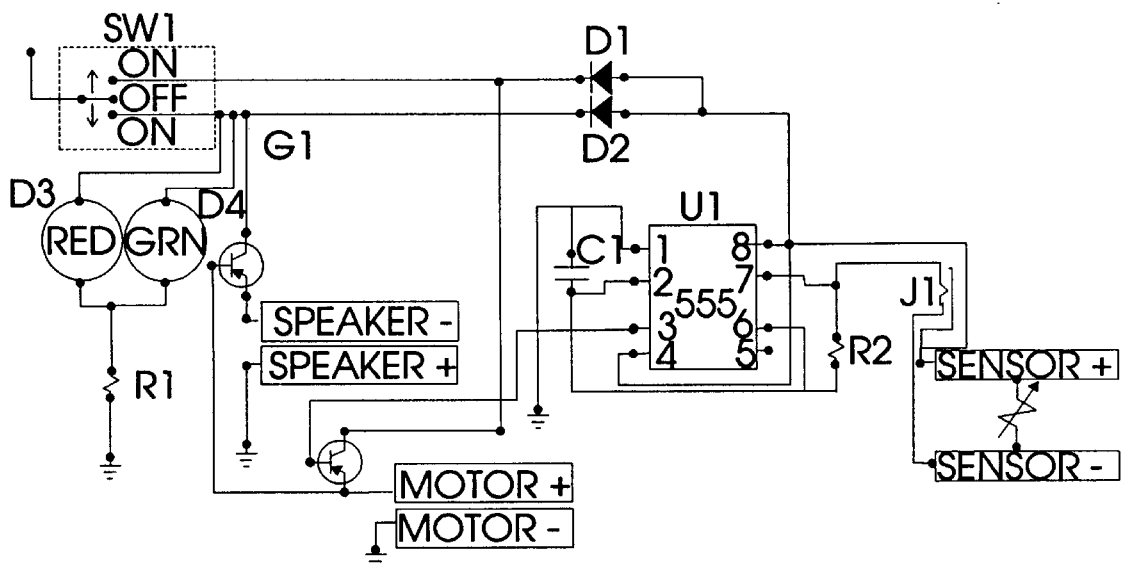
FIGURE 5
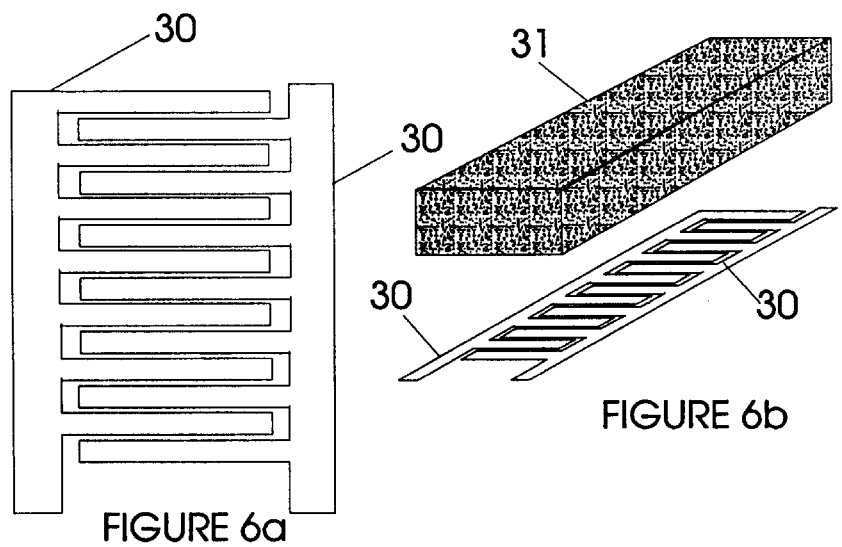
FIGURE 6a
FIGURE 6b

POSITION SENSING AND SIGNALING SYSTEM

BACKGROUND OF THE INVENTION

1. Field of the Invention

This invention relates to bio-feedback devices used by individuals to monitor and control various physical characteristics or states of the anatomy. More specifically the instant invention relates to a biofeedback device, incorporating a variable resistance sponge, sensitive to small changes in pressure, utilized for sensing various positions of the Transverse Abdominis Muscle (TAM) and thereby permitting of individuals wearing the device to improve posture and abdominal strength.

2. Description of Related Art

The related art is replete with devices used for measuring displacement of abdominal muscle position, these include U.S. Pat. No. 4,801,921 to ZIGENFUS, U.S. Pat. No. 4,846,462 to REGNIER et.al., U.S. Pat. No. 4,846,157 to SEARS and U.S. Pat. No. 5,161,543 to ABRAMSON. A distinguishing feature of these devices is the nature of sensor and the signal used to alert the user. In ZIGENFUS there are no sensors at all instead a constant signal is applied to the abdominal wall to remind the wearer to contract the abdominal muscles. The signal is of fixed frequency. However, pitch may be adjusted. In REGNIER the sensor is a lever which activates a variable potentiometer. When movement of the potentiometer reaches a given set point an audible fixed electric signal is generated. SEARS teaches a belt driven device like REGNIER however, SEARS utilizes a simple magnetic switch mounted on an elastic portion of a belt. The closure of the switch occurs on stretching of the elastic and causes an electrical circuit to generate an audible signal. ABRAMSON discloses a sensing device which comprises a pressure sensor, the character of which is not specified, which when activated produces an alarm.

Human beings are subject to habitation and so prior art devices which depend on a set signal at a set point (a result in prior art devices due to the difficulty of measuring small mechanical movement of body parts) may be ignored by the individual wearing such devices. The instant invention provides a variable pitch signal directly related to the degree of relaxation of the TAM and thus permits a range of signal proportional to the range of excursion of the abdominal wall thereby facilitating a range of bio-feedback cues which are not subject to habitation. Of interest is U.S. Pat. No. 3,648,686 to PAYNE which shows an electrical circuit for generating a variable pitch signal in response to galvanic skin response changes and includes a pair of electrodes used to sense changes in skin resistance. No variable resistance sensor is incorporated into the device nor is such sensor activated by physical pressure although psychological pressure may indeed be measured. PAYNE does not show who to measure small excursions of physical elements no how these would be used to aid in control of the TAM.

SUMMARY OF THE INVENTION

Exercise of Transverse Abdominis Muscle (TAM) has generally been ignored by the exercise industry. Set ups and "crunches" do not exercise the TAM which is the only muscle which can constrict the size of the abdomen. However, when the TAM is constricted very small travel of the abdominal wall is actually realized. In order to sense such travel without complex mechanical linkages, it was discovered that anti-static foam is very sensitive to changes in its shape and could be used in some form to detect such small changes.

Anitstats or ESD protective foam has been utilized for a variety of purposes in the electronics industry particularly in the handling and packaging of electronic devices and business machine components. This has lead to a steady growth in the use of antistatic coatings as well as internal antistat additives as is typified by U.S. Pat. No. 4,1818,437 to WILEY and U.S. Pat. No. 5,076,967 to TOJO. These devices which may be based on either polymer, resin, rubber or other flexible material and take on the form of a sponge, foam or other structure which exhibits a generally uniform resistance to bleeds off any charge buildup on electronic devices the pins of which have been embedded in such foam and prevents destruction of internal connections of integrated circuits. Such foam is usually of very high uniform resistance as shown in TOJO which discusses resistance in the range of $10^5$ to $10^{11}$ ohms per centimeter but may be made to exhibit low resistance levels in the range of a single ohm as well as shown in WHILEY. The production of such antistatic devices is well known in the art and the availability of such devices either as a mat, foam or sponge is common throughout the electronics industry. While a broad range of resistances exists, it was intended that such foam exhibit uniform resistance characteristics to provide a predictable resistance to discharge electrostatic Charges. It was not anticipated that a continuously variable resistance over a specific range was achievable in electronic circuits with such foam. Each of these ESD devices to the extent that they are flexible or resilient to some degree are referred to herein as an antistatic foam.

It has been discovered that manipulation of such antistatic foams or even a change in its environment can change the resistance characteristics thereof. There have been several prior art devices which provide a variable resistance, in addition to the well known rotatable and slide potentiometer. These have taken the form of pressure sensitive conductive rubbers which contain suspended carbon or conductive metal particles these have been of the switching type and were designed to present only two conductive states. These cannot be used as sensors because they cannot be used to sense intermediate values. For example when the antistatic foam of the instant invention is compressed the resistance changes. That is, a decrease in the outer dimensions of the foam reduced the internal resistance thereof. It has been determined that typical antistatic foam has a very high resilience. The change in resistance of the foam is determined by the amount of pressure exerted on it or as is noted below by the degree of change in humidity. As is demonstrated by the examples which follow.

Addition of electrodes to the foam forms a sensor which permits sensing of any change which compresses the foam or which changed the specific environment. The sensor element includes a plurality of interlaced electrodes in juxtaposition with the antistatic foam which minimizes hysteresis apparent in other devices described below. A single point or plate can result in slippage as discussed in U.S. Pat. No. 5,336,442 to KURAMOCHI. KURAMOCHI indicates that a rubber sensor (not of the ESD type) having a conductive filler in oil, which is capable of sensing intermediate changes of resistance, is disclosed in Japanese Patent Publication No. Sho 60-33138, but is subject to slippage which creates hysteresis.

KURAMOCHI is itself of interest in that it discloses a conductive rubber capable of a decrease in electrical resistance on stretching and which discloses that a uniform change in resistance by compression or stretching of ESD foam not possible.

A particular preferred implementation of the instant invention is in the form of a two pole sensor incorporated into a bio-feedback monitor. The Transversus Abdominis Muscle runs transversely of the longitudinal axis of the body. This muscle is crucial to proper posture and low back problems. None of the regularly prescribed exercises for strengthening the abdomen and the lower back specifically address the Transversus Fibers. In fact, standard "sit-ups" or "crunches" do not require any contraction of this muscle. However, an individual may contract this muscle voluntarily by "sucking in the stomach." The contracting of the TAM muscle causes the muscle to hypertrophy which results in increased strength and tone of the muscle. However, this activity is subject to habituation and will cause one to stop concentrating and relax the muscle unless some way of maintaining awareness is achieved. The two pole sensor may be used for this purpose and is physically attached to the monitor which can be worn on the belt or at or near the waist line. Since the contraction of the TAM causes a decrease in diameter of two to three inches, the actual contraction at any given point is actually very small. Accordingly, position at the abdominal wall is not crucial. What is essential is that the monitor should be able to fall away from an overhanging or pendulous abdomen. This is accomplished by the use of an elongated belt clip which tends to find its own "best position" with very little adjustment from the wearer. A lever on the back of the monitor rests against the body and engages the sensor comprising a variable resistance component. This sensor must be highly sensitive to pressure changes and cause the full range of electronic operation of the monitor with little actual mechanical movement. In this case, the variable resistance component is the antistatic foam, which with the electrodes forms the variable resistance in an electrical circuit. When pressure is exerted against the lever, it causes a significant change in resistance with very slight movement and energizes the electrical circuit above a given threshold and causes a variable pitch and a variable volume sound to be generated or alternatively drives an electrical vibrator motor at a variable speed. The variation in pitch or vibrator speed is directly related to the amount of pressure exerted on the lever.

The biofeedback device is adapted so that the lever including the foam sensor may be bypassed or removed and a variety of different devices also utilizing a foam sensor may attached or otherwise interconnected to the electrical circuit in place of the lever to be utilized for other purposes. One of these is a intravaginal sensor which may be used to sense pressure exerted when performing constrictor muscle exercises such as the Kaegel exercise to correct urinary incontinence.

An Alternative embodiment is to use the sensor as a mask or a small section thereof positioned near the nostrils or mouth to intercept the breathing of a patient or otherwise position the sensor in some other environment which exposes the sensor to a change in humidity. On a change of humidity such as is encountered in the course of inhaling and exhaling, the sensor decreases resistance when the humidity increases in the same manner as when the sensor is physically compressed. The change in humidity will then operate the electrical circuit in the same manner as in the change in pressure to detect apnea or the cessation of breathing or a change in respiratory rate.

While a variety of variable resistance devices are available, it has been discovered that the resistance foam utilized for anti-static transport and storage of integrated circuits is a low cost reliable source of variable resistance. The electrical circuit described detects a change in resistance of the foam in response to physical pressure exerted on the lever which in turn compresses the foam as the muscles in the abdominal wall are relaxed.

In the case of the constrictor muscle pressure exerted by tensing of the muscles compresses the foam surrounding the electrodes thereby varying the resistance in relation to small physical travel with the same result as in the lever driven version.

BRIEF DESCRIPTION OF THE DRAWINGS

FIG. 3 is an exploded view of the lever mechanism.

FIG. 4a is a view of the cylindrical form of a two pole sensor.

FIG. 4b is a view of the cylindrical two pole sensor enclosed in a water proof container.

FIG. 5 is a circuit diagram of the electrical circuit of the device.

FIG. 6a is a form of the electrodes for a two pole sensor.

FIG. 6b is a view of the antistatic foam positioned above the electrodes for a two pole sensor.

DESCRIPTION OF THE PREFERRED EMBODIMENT(S)

Figure 1:
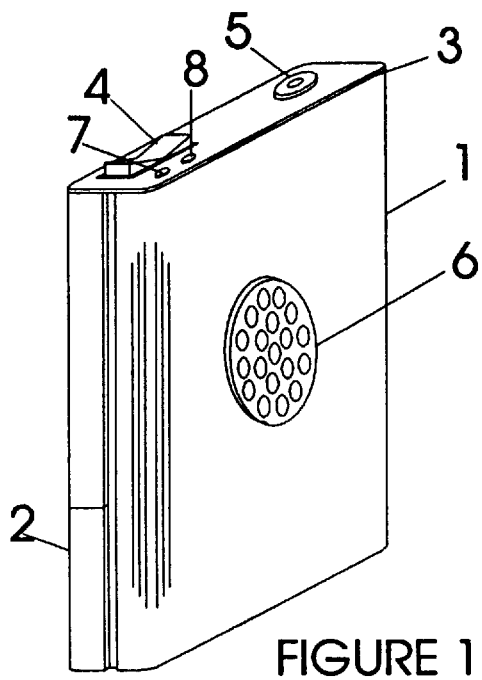
FIG. 1 is a perspective view of the side and front of the device.

With reference to the drawings, FIG. 1 shows an outer case or housing 1, having a rear cover 2, which permits the insertion of a battery 10 inside the housing 1 and a top 3 which supports a switch 4 and a jack 5 for receiving alternative pressure sensors. In the front of housing 1 is a speaker 6 which provides the variable pitch sound. The variable speed vibrator motor (not shown) is mounted inside the housing directly on a circuit board which supports the electrical circuit for the device as shown in FIG. 5. The switch 4 is a single pull double throw rocker switch with a center off position and may be set to the speaker mode, the vibrator mode or centered to the off position a red diode 7 and a green diode 8 are energized when set to the speaker mode and the vibrator mode respectively.

Figure 2:
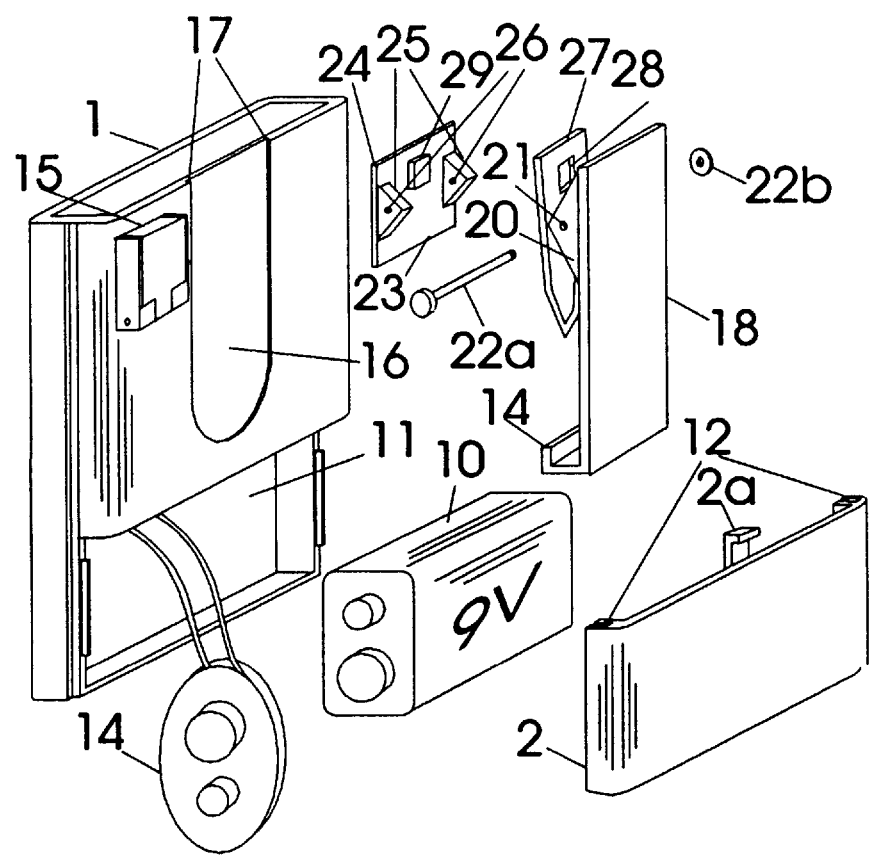
FIG. 2 is an exploded view of the back and side of the device omitting the top.

FIG. 2 shows the side and rear of housing 1, with the rear cover 2 and the belt attachment 9 exploded. Removal of the rear cover shows a cavity 11 inside the housing 1 for receiving a nine volt battery 10. The rear cover 2 has a tang 2a with a protruding end for engagement with a notch inside of housing 1, and a pair of grooves 12 on each side thereof for engagement with a pair of flanges 13 mounted on the side walls of the cavity 11 adapted for receiving the grooves of rear cover 2. A battery connector 14 is fastened inside the cavity 11 and is adapted for receiving the battery 10 which provides the power for the device.

FIG. 2 also shows a sense lever mechanism 15 mounted on the rear of the housing 1 near the top thereof. An elongated grove 16 is provided at the top of the housing 1 which extends parallel to the vertical axis of the housing 1. The grove 16 has a pair of angular recesses 17 on each side thereof.

The belt attachment comprises an elongated belt lever 18 having a hooked end 19 at the bottom thereof for engaging a belt and a pair of angular flanges 20 on each side thereof at the top of said lever 18. Each of the angular flanges 20 has a hole 21 in the side thereof for receiving a first pin 22a having a head on one end and an annular grove for receiving a fastener 22b on the other. The belt lever is attached to a belt lever mount 23, which has angled sides 24 adapted for insertion into the grove 16 and engaging the angular recesses 17. The tolerances should be sufficiently close to permit vertical movement of the belt lever mount 23 by hand but providing sufficient friction to remain in place while worn. The belt lever mount 23 also has a pair of angular flanges 25 mounted on each side thereof but disposed inwardly relative to the angular flanges 21 of the belt lever 18. The angular flanges 25 each have a hole 26 in the side thereof for receiving the first pin 22a. The belt lever 18 and the belt lever mount 23 are rotatable attached by engagement of first pin 22a through holes 21 and 26. First pin 22a is held in place by a fastener 22b on one end thereof. Interposed between the belt lever 18 and the belt lever mount 23, is a spring 27. Spring 27 has a rectangular hole 28 adapted for receiving a rectangular flange 29 centrally mounted at the top of belt lever mount 23. Spring 27 exerts pressure at the top of the belt lever 18 and the belt lever mount 23 and biases the hooked end 19 of the belt lever 18 against the housing 1.

FIG. 3 shows the sense lever mechanism 15 in an exploded form. The lever mechanism may be removable to a permit attachment of a variety of sensors directly to the circuit in place of the jack 4. The sensor configuration is shown in FIGS. 6a and 6b and utilizes a plurality of interlaced flexible electrodes 30, electrically isolated from opposite polarities, except through the foam, which are maintained in contact with the antistatic foam 31 such that electrical conduction is permitted between opposite electrodes. The particular foam used in this sensor is Phillips ECG #ASTAT-12 although other types of foam may be used with an appropriate adjustment in the circuit component values. The resistance of this foam is in excess of 2 Megohms without pressure of the electrodes against the foam. The ESD foam resistance varies dependent upon the physical dimensions thereof as well as its chemical composition as noted above. Generally, the larger the dimensions of the foams, the greater the resistance of the foam. Compression testing of a ¼ piece of the Phillips foam described above yielded the data in Table I. This data is illustrated in graphical form in FIG. 9.

Figure 9:
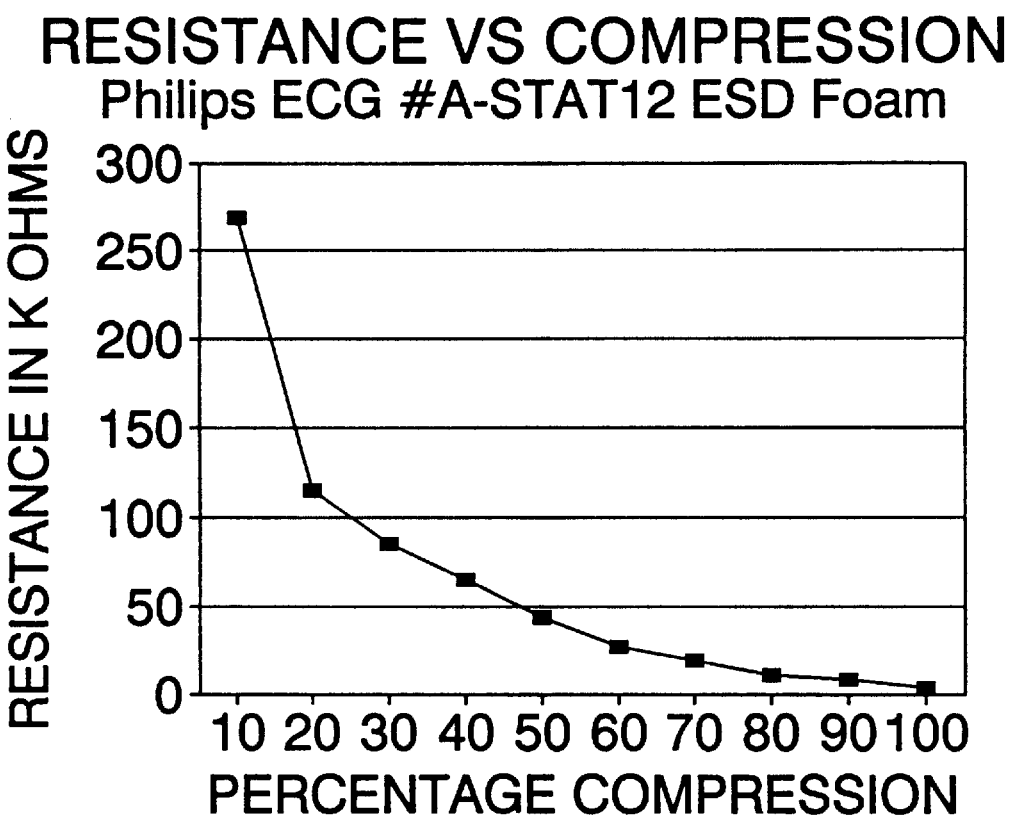
FIG. 9 is a graph of the data in Table I.

As can be seen by FIG. 9 as the foam was compressed, the resistance thereof in the direction of compression decreased. After removing the compression permitted the resilient foam to return to its former dimensions almost immediately. Extended compression, however, results in a longer time for the foam to return to its former dimensions. However, the upper range of the resistance curve was temporarily shifted approximately 30% higher after compression. Over time the resistance of this upper portion of the resistance curve also returned to its original characteristics. In fact almost any manipulation of the foam such as bending piece being measured caused a reduction of the resistance of the foam in response to the manipulations. Since various types of ESD foam have different ranges of resistance, many types may be incorporated into a variety of electrical circuits upon proper resistance range selection and the invention is not restricted to the specific foam used in the preferred embodiment. Accordingly, when the foam is provided with electrodes and a source of variable pressure act it acts as a variable resistor or a very low cost potentiometer. The foam was also tested using humidity. The presence of a humid environment to the ESD foam caused the resistance to decrease. The absence of a humid environment caused the resistance of the foam to return to the level of resistance which existed at ambient ie.

increase. Accordingly, when electrodes are attached to the foam sensor, it may also be used to detect change in humidity conditions. When used as a sensor positioned under the nose of a human subject the specific breathing patterns are detected. Applying water to the foam also caused a decrease in resistance of the foam from dry conditions. On drying the resistance returned to normal. Other changes in the environment of the foam may also cause a change of the resistance and are considered within the course and scope of the invention.

The resistance characteristics of such foam when pressure is applied is shown in Table I below.

TABLE I

| Resistance K Ohms | Percentage Compression | Settling Range K Ohms | Dimension of package | After Compression Resistance K Ohms |
| --- | --- | --- | --- | --- |
| 2,000+ | 0% | N/A | .427" | |
| 269 | 10% | 272–263 | .402" | |
| 115 | 20% | 118–114 | .377" | |
| 85 | 30% | 86–82 | .352" | Sample |
| 65 | 40% | 66–61 | .327" | 94.2 |
| 44 | 50% | 45–43 | .302" | |
| 27 | 60% | 27–25 | .277" | Sample |
| 19 | 70% | 19–19 | .252" | 23.8 |
| 11 | 80% | 11–10 | .227" | |
| 8.36 | 90% | 8.38–8.33 | .202" | |
| 3.74 | 100% (Est) | 3.75–3.73 | .177" | |

Interlaced electrodes were placed on each side of the foam and both leads were tied together to take electrical measurements. The electrodes were each etched on a circuit board section which was 0.08" and 0.097" inches in width respectively therefore the entire test package was 0.427" in height with the 0.25" section of foam in the center. This permitted equal compression of the foam on the test piece. The range of settling exhibited as shown in Table I was also observed with ordinary potentiometers. The foam also changes resistance on pressure in the direction of pressure while resistance in other directions remains unaffected. A piece of the Phillips foam described above having a length of 1.75" and a width of ⅝" was subjected to 50% pressure in the center thereof with a probe. The resistance measured was 55K Ohms on release the resistance of the test sample was again measured at 50% compression and the sample had increased to 74K Ohms. Resistance in other dimensions remained unchanged. However, as the size of the sample changes resistance in other dimensions may be affected. This same sample size was used for a breath test and resistance changed approximately 10K Ohms from ambient in response to breath moisture. The resistance generally of the Phillips foam was approximately 160K Ohms per inch between probes inserted into the ESD mat. It was discovered that different areas of a commercially available ESD mat material may have slightly different resistance values. While the particular foam discussed caused a decrease in resistance when compressed it is clear that foam which results in an increase in resistance on compression is also available dependent on its chemical composition as noted herein.

It was determined that the interlaced electrode configuration ensures that pressure substantially anywhere on the foam causes a change in the current between the electrodes and thus activates the circuit. In this form of the embodiment the foam 31 is placed between the lever 33, as shown in FIG. 3, such that when pressure is exerted against the lever 33 by relaxation of the diaphragm muscles the foam 31 is compressed by a button 34. A moisture proof diaphragm 35 made of rubber or other suitable moisture resistant material is placed between the foam 31 and the button 34 to minimize moisture entering into the sensor. The lever 33 is mounted on a housing 36 which has an opening 37 therein for receiving the body of the lever 33. The upper portion of the housing has a smaller opening 38 for receiving the top of the lever 33. The housing 36 has a pair of holes 39 for receiving a second pin 40a having a head on one end and an annular grove for receiving a fastener 40b on the other. The upper portion of the lever 33 has a head 41 adapted for insertion into the opening 38 which has a hole 42 for receiving second pin 40a. A flexible stop 43 is mounted on top of lever 33 and prevents lever 33 from fully opening inadvertently by engaging the housing 1. Housing 35 also has a rectangular hole 44 in the center thereof which permits the foam 31 to engage the electrodes 30 (not shown) which may be mounted directly on the circuit board of housing 1.

An alternative form of the sensor is shown in FIGS. 4a & 4b. The sensor has a plurality of interlaced electrodes 30a which generally enclose a flexible insulated cylindrical core 46. The foam 31a is then wrapped about this cylinder of interlaced electrodes. The foam 31a is then enclosed in a water proof enclosure 47 suitable for keeping body fluids and other substances out of contact with the foam 31a or the electrodes 30a. This sensor may then be inserted into the body cavity. Constrictor muscle compression during Kaegel exercise will then operate the device in the same manner as the lever model.

FIG. 5 is an electrical schematic of the sensing circuitry. A source of power is represented by the – sign which corresponds to the – pole of battery 10. The ground symbol corresponds to the + pole of the battery 10. Switch 4 is represented by SW1. The switch SW1 has two independent ON positions. In the down position relative to the schematic of FIG. 5 electrical connection is established to three paths. The first is through a green LED D4 and a restor R1 to ground. This illuminates the green diode and shows that the speaker portion of the circuit is ready. The next connection from the switch to the collector of a PNP transistor G1. The emitter of G1 is connected to one pole of the speaker. The other side of the speaker is connected to ground. The base of transistor G1 is connected to pin 3 of a 555 timer integrated circuit U1. The next connection from the switch in the down position is to the emitter of diode D2 the collector of diode D2 is connected to pin 8 and 4 of and to the – side of the sensor which is shown as a variable resistor in the schematic. The + side of the sensor is connected to resistor R2 and to pin 7 of U1. The + or opposite side of resistor R2 is connected to pin 6 and pin 2 of U1 and the – side of capacitor C1. The + side of capacitor Cl is connected to ground and pin 1 of U1. When the resistance across the electrodes of the sensor decreases, the current increases and U1 begins oscillation. The greater the current the greater the oscillation. This applies a signal to the base of G1 which is amplified and applied to the speaker thereby causing a variable pitch sound to be generated for bio-feedback control.

When the switch SW1 is in the up position relative to the schematic position electrical connection is also established along three paths. The first is through a red LED D3 and a restor R1 to ground. This illuminates the red diode and shows that the vibrator motor portion of the circuit is ready. The next connection from the switch is to the collector of a PNP transistor G2. The emitter of G2 is connected to one pole of the vibrator motor. The other side of the motor is connected to ground. The base of transistor G2 is connected to pin 3 of U1. The next path from the switch in the up position is to the emitter of diode D1 the collector of diode D1 is connected to pin 8 and 4 of and to the – side of the sensor 30 shown as a variable resistor. The + side of the sensor is connected to resistor R2 and to pin 7 of the 555 integrated circuit. The + or opposite side of resistor R2 is connected to pin 6 and pin 2 of U and the – side of capacitor C1. The + side of capacitor C1 is connected to ground and pin 1 of U1. When the resistance across the electrodes of the sensor decreases, the current increases and U1 begins oscillation. The greater the current the greater the oscillation. This applies a signal to the base of G2 which is amplified and applied to the vibrator motor thereby causing a variable speed vibration to be generated for bio-feedback control. Table II shows the specification of each of the elements of the electrical circuit described above in the preferred embodiment.

TABLE II

| | |
|---|---|
| SW1 | SPDT center off |
| R1 | 2.2K Ohms |
| R2 | 50K Ohms |
| D1 | 1N4001 |
| D2 | 1n4001 |
| D3 | P363-ND RED LED |
| D4 | P364-ND GREEN LED |
| G1 | PNP |
| G2 | PNP |
| C1 | .033 micro farads |
| U1 | LM555 Timer |
| J1 | Jack ⅛" mini jack |
| Speaker | Piezo 273-091 Radio Shack |
| Motor | 270 DC Motor 1.3 volts (Autotrol Corporation) |

(All resistors are ¼ watt)

The speaker draws current of about 4 microamps at intermediate depression and 200 microamps on full depression. The motor draws 40 ma at 0.68 volts (intermediate depression) and 50 ma at 0.78 volts (full depression). Table IIl shows the status of various electrical current levels through the foam when in standby mode and when in operation with a battery level of 9.05 Volts which provides 0.650 amp hours.

TABLE III

| Audio Circuit | | Vibrator Circuit | |
|---|---|---|---|
| Standby | 9.81 mA | Standby | 7.12 mA |
| Full Depression | 330 mA | Full Depression | 50 mA |
| Half Depression | 250 mA | Half Depression | 40 ma |

Figure 7:
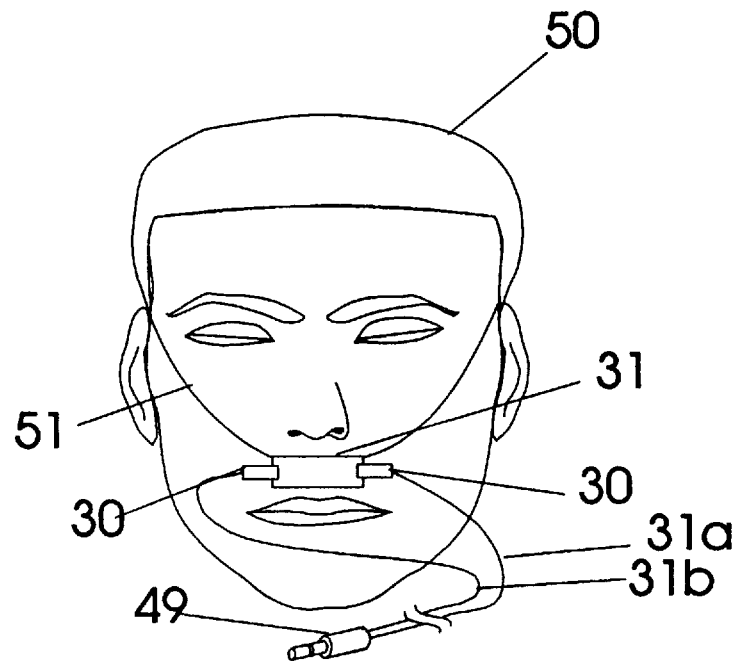
FIG. 7 is a frontal view of the sensor in position to monitor breathing.

Aa seen in FIG. 7, an alternative sensor is in the form of a small piece of foam 31 shown having electrodes 30 attached on opposite sides thereof which may be positioned directly beneath the nostrils of a patient 50. It may be attached by adhesive or by an elastic strap 51 to secure it in position under the nose. The electrodes 30 are connected to a pair of leads 31a which are connected to plug 49 which is a commonly available two contact plug. The sensor is in the path of the patients breath and may be utilized to sense the change in humidity on inhaling and exhaling. This permits the monitoring of babies breathing patterns to aid in the prevention of Sudden Infant Death Syndrome (SID or other respiratory rate changes which imply deteriorating conditions of any patient 50 and permit early intervention by medical personnel. The sensor may also be incorporated into a mask which is placed over the patient's nose and mouth, however, the mask must permit free breathing by including holes in the foam to minimize carbon dioxide buildup or obstruction to breathing. The electrodes in this case are simply metallic clips clipped to the foam.

Figure 8:
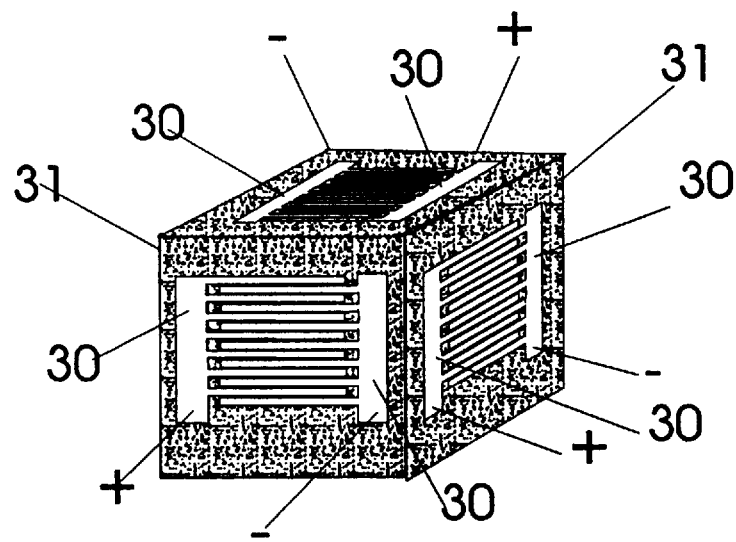
FIG. 8 is a multiple dimension version of the foam sensor.

The foam 31 may be utilized to create multiple sensors in a single piece of foam as is shown in FIG. 8. The three dimensional nature of the foam permits the addition of a plurality of electrode pairs about the surface of the foam 31. With reference to FIG. 8, an electrode pair 30 may be placed on the sides of the foam 31, on the bottom thereof and on the ends of the foam. A pressure point in any one direction will not affect the resistance in any other direction. For example, such a sensor can be included in a joy stick which will permit the sensing of changes in direction of motion of the a joy stick in the up/down, forward/reverse and left/right directions, permitting display of x,y motion on a video screen as well as a variable trigger option or other function.

While the device has been described in a number of applications which utilize a pressure to change the resistance and therefore the frequency of response generated by the electrical circuit, it is clear that minor modifications to the circuit can result in a release of pressure to change the resistance and therefore the frequency of response.

Having thus described the invention what is claimed is:

1. A signaling device comprising:
   a. a first housing,
   b. an elongated first lever having a hooked end, attached to said first housing and disposed in a downward direction with respect thereto,
   c. a sense lever mechanism attached to said first housing, having a sense lever rotatably attached thereto, said sense lever disposed in an upward direction with respect to said first lever,
   d. an electrical circuit disposed in said first housing, electrically coupled to a variable resistance element, said circuit and adapted for generating a signal on a change in resistance of said variable resistance element, said variable resistance element comprising a single layer of electrostatic foam, adapted for changing resistance on compression, said resistance element disposed between said sense lever and said housing,
   e. at least one pair of opposite polarity electrodes electrically coupled to said electrical circuit and adapted for engaging one side of said variable resistance element,
   f. means for converting said signal from said electrical circuit into a selected physical signal, and
   g. means for selecting said selected physical signal,
whereby movement of said second lever compresses said foam and causes said circuit to generate a signal on change in resistance of said foam tbereby generating said selected physical signal.

2. A signaling device as described in claim 1 wherein said electrical circuit includes a variable frequency oscillator for generating a variable frequency signal said electrical circuit adapted to generate a signal having a variable frequency and amplitude output signal based on said oscillator signal.

3. A signaling device as claimed in claim 1 wherein said electrodes coupled to said circuit said electrodes in the form of a plurality of generally parallel interlaced electrode elements disposed between generally parallel electrode elements of the opposite polarity electrode and spaced apart therefrom for engaging said single layer of electrostatic foam.

4. A signaling device as described in claim 3 further comprising a speaker electrically coupled to said circuit adapted for generating sound waves of variable pitch and volume in proportion to the change in resistance of antistatic foam when selected by said selection means.

5. A signaling device as described in claim 3 further comprising a vibrator motor electrically coupled to said circuit adapted for generating vibration waves variable in frequency and intensity in proportion to the change in resistance of said antistatic foam when selected by said selection means.

6. A signaling device comprising:
   a. a first housing,
   b. an elongated first lever, attached to said first housing and disposed in a downward direction with respect thereto,
   c. a sense mechanism attached to said first housing,
   d. a sense lever rotatably attached to said sense mechanism having a button thereon disposed toward said first housing, said sense lever disposed in an upward direction with respect to said first lever,
   e. an electrical circuit disposed in said first housing adapted for generating a signal on change in resistance of a variable resistance element coupled to at least one pair of opposite polarity electrodes electrically coupled to said electrical circuit adapted for coupling with variahle resistance element said variable resistance element comprising a single layer of electrostatic foam, adapted for changing resistance on compression, disposed between said second lever and said housing and engaging one side of said foam,
   f. means for converting said signal from said electrical circuit into a selected physical signal, and
   g. means for selecting said selected physical signal.

7. A variable resistor comprising:
   a. a layer of conductive material comprising a single layer of antistatic foam adapted to change resistance on change in at least one physical dimension, and
   b. two electrodes having a plurality of interlaced leads each lead disposed between and spaced apart from leads of opposite polarity of both electrodes in juxtaposition with one side of said layer of conductive material.

8. A variable resistor comprising:
   a. a layer of conductive material comprising a single layer of antistatic foam adapted to change resistance on change in at least one physical dimension, and
   b. at least two electrodes in juxtaposition with said antistatic foam which electrodes each comprise a grid of interlaced electrode elements, said grid comprising a plurality of generally parallel elongated conductive elements interposed between and spaced apart from generally parallel conductive elements of the electrode of the opposite pole, said electrode grid disposed in juxtaposition with one side of said antistatic foam layer such that when said antistatic foam is deformed at least two electrode elements of the grid of said electrodes of opposite poles will engage said conductive material at a point along the length of said elements and exhibit a variable resistance between them.

9. A variable resistor comprising:
   a. a resistive foam adapted to change resistance on change in any physical dimension, and
   b. a plurality of pairs of electrodes of opposite polarity each pair of electrodes in juxtaposition with different sides of said foam.

10. A signaling device as described in claim 1 wherein said apparatus for converting said electrical signal into a physical signal further comprises a sound generating device adapted for creating sound waves which vary in frequency and amplitude in proportion to said electrical signal.

11. A signaling device as described in claim 1 further comprising a vibrating device adapted for creating vibration waves proportional to said electrical signal.

12. A transverse abdominis muscle position signaling device comprising:
   a. a housing,
   b. an electrical circuit disposed in said housing adapted for generating a signal having a variable amplitude and a variable frequency component,
   c. position sensing means coupled to said housing and adapted to be disposed in juxtaposition with the abdominal wall and moveable in response to a change in position of the transverse abdominis muscle on excursions of the abdominal wall,
   d. variable resistance means electrically coupled to said electrical circuit for sensing movement of said position sensing means and causing said electrical circuit to generate said signal,
   e. at least one pair of opposite polarity electrodes electrically coupled to said electrical circuit adapted for coupling with said variable resistance means,
   f. means for converting said signal from signal electrical circuit into a selected physical signal, and
   g. means for selecting said selected physical signal.

13. A signaling device as described in claim 12 wherein said variable resistor comprises:
   a. an antistatic foam component adapted to change resistance on change in at least one physical dimension, and
   b. at least two electrodes in juxtaposition with said antistatic foam.

14. A signaling device comprising:
   a. a first housing,
   b. an elongated first lever, having a hooked end, rotatably attached to said first housing adapted for engaging a belt and disposed in a downward direction with respect thereto,
   c. a sense mechanism attached to said first housing,
   d. a sense lever rotatably attached to said sense mechanism having a button thereon disposed toward said first housing, said sense lever disposed in an upward direction with respect to said first lever;
   e. an electrical circuit disposed in said first housing adapted for generating a signal on a change in resistance, and
   f. at least one pair of opposite polarity electrodes electrically coupled to said electrical circuit adapted for coupling with said resistance element on one side of said foam,
   h. a resistance element electrically coupled to said electrical circuit for sensing a change in position of said sense lever and causing said electrical circuit to generate said signal, said sensor further comprising a single layer of electrostatic foam, adapted for changing resistance on compression, disposed between said second lever and said housing and engaging said electrodes and generating a variable resistance when at least a portion of said variable resistance foam is electrically coupled to said electrodes electrically connected to said circuit,
   i. means for converting said signal from said electrical circuit into a selected physical signal, and
   j. means for selecting said selected physical signal,
   k. apparatus for converting said electrical signal into a selected physical signal.

15. A signaling device as described in claim 14 further comprising a sound generating device adapted for creating sound waves proportional to said amplitude and frequency components of said electrical signal when selected by said selecting means.

16. A signaling device as described in claim 14 further comprising a sound generating device adapted for creating vibrational waves proportional to said amplitude and frequency components of said electrical signal when selected by said selecting means.

17. A signaling device as claimed in claim 14 wherein the position of said first lever is adjustable with respect to said first housing at the point of attachment of said first lever to said first housing.

18. A variable resistor as described in claim 8 wherein said single layer of antistatic foam forms a hollow cylinder, and said electrode grids form a generally cylindrical structure with a plurality of the electrode elements of each such grid curved to be disposed between and spaced apart from electrode elements of the grid of opposite polarity adapted for electrical coupling to said antistatic foam cylinder.

19. A variable resistor as described in claim 9 wherein said pairs of electrodes comprise a plurality of elongated electrode elements of one polarity disposed between and spaced apart from elongated electrode elements of said opposite polarity electrode of said pair for engaging said sides of said foam.

* * * * *